(12) United States Patent
Lu

(10) Patent No.: US 12,053,638 B2
(45) Date of Patent: Aug. 6, 2024

(54) PROPHYLACTIC TREATMENT FOR MIGRAINE HEADACHES

(71) Applicant: Aruene Corporation, Wilmington, DE (US)

(72) Inventor: Ting W. Lu, Cupertino, CA (US)

(73) Assignee: Aruene Corporation, Wilmington, DE (US)

( * ) Notice: Subject to any disclaimer, the term of this patent is extended or adjusted under 35 U.S.C. 154(b) by 63 days.

(21) Appl. No.: 16/773,670

(22) Filed: Jan. 27, 2020

(65) Prior Publication Data

US 2020/0155866 A1 May 21, 2020

Related U.S. Application Data

(63) Continuation of application No. 15/831,795, filed on Dec. 5, 2017, now abandoned, which is a continuation
(Continued)

(51) Int. Cl.
*A61N 2/02* (2006.01)
*A61N 2/00* (2006.01)
(Continued)

(52) U.S. Cl.
CPC ............ *A61N 2/008* (2013.01); *A61N 2/006* (2013.01); *A61N 2/02* (2013.01); *G16H 20/40* (2018.01);
(Continued)

(58) Field of Classification Search
CPC ........... A61N 2/006; A61N 2/008; A61N 2/02
See application file for complete search history.

(56) References Cited

U.S. PATENT DOCUMENTS 6,402,678 B1  6/2002 Fischell et al.
6,547,713 B1 * 4/2003 Talpo ..................... A61N 2/02
                                                          600/9
(Continued)

FOREIGN PATENT DOCUMENTS

CN        104093448 A    10/2014
EP          1977787 A1   10/2008
(Continued)

OTHER PUBLICATIONS

Anatomy of a Migraine—Part 1: The Prodrome and Aura [webpage], retrieved from the Internet:< http://headaches.about.com/cs/headpain101/a/anatomy_mig.htm>, updated Jan. 9, 2008, 2 pages total.
(Continued)

*Primary Examiner* — Christine H Matthews
(74) *Attorney, Agent, or Firm* — DLA Piper LLP (US)

(57) ABSTRACT

A treatment apparatus configured to treat a patient for a neurological disorder comprises a patient interface configured for the patient to enter data for an assessment of his or her subjective sensations, for example pain symptoms associated with migraines. The subjective patient sensation data may comprise at least one of a patient symptom of the neurological condition or a patient trigger of the neurological condition. For example the subjective patient sensations may comprise symptoms that correspond to migraine such as aura symptoms. The treating physician can view the subjective patient data, and diagnose and treat the patient with a treatment plan by writing a treatment plan to a storage device, for example treatment instructions written to a smart card. The storage device can be delivered to the treatment apparatus such that the patient can be treated in response to physician's treatment plan.

9 Claims, 11 Drawing Sheets

Related U.S. Application Data of application No. 15/285,249, filed on Oct. 4, 2016, now abandoned, which is a continuation of application No. 12/718,163, filed on Mar. 5, 2010, now Pat. No. 9,492,680.

(60) Provisional application No. 61/158,087, filed on Mar. 6, 2009.

(51) Int. Cl.
*G16H 20/40* (2018.01)
*G16H 20/70* (2018.01)
*G16H 40/63* (2018.01)
*G16Z 99/00* (2019.01)

(52) U.S. Cl.
CPC ............. *G16H 20/70* (2018.01); *G16H 40/63* (2018.01); *G16Z 99/00* (2019.02)

(56) References Cited

U.S. PATENT DOCUMENTS

| | | | |
|---|---|---|---|
| 7,223,234 | B2 | 5/2007 | Stupp et al. |
| 7,294,101 | B2 | 11/2007 | Fischell et al. |
| 9,492,680 | B2 | 11/2016 | Lu et al. |
| 2001/0051819 | A1 | 12/2001 | Fischell et al. |
| 2001/0056290 | A1 | 12/2001 | Fischell et al. |
| 2002/0002390 | A1 | 1/2002 | Fischell et al. |
| 2003/0028072 | A1 | 2/2003 | Fischell et al. |
| 2003/0088290 | A1 | 5/2003 | Spinelli et al. |
| 2003/0120324 | A1 | 6/2003 | Osborn et al. |
| 2004/0122281 | A1 | 6/2004 | Fischell et al. |
| 2004/0153129 | A1 | 8/2004 | Pless et al. |
| 2004/0181115 | A1 | 9/2004 | Sandyk et al. |
| 2004/0181262 | A1* | 9/2004 | Bauhahn ............ A61N 1/36071 607/48 |
| 2004/0249422 | A1 | 12/2004 | Gliner et al. |
| 2005/0086082 | A1 | 4/2005 | Braunstein et al. |
| 2005/0131739 | A1 | 6/2005 | Rabinowitz et al. |
| 2005/0234286 | A1 | 10/2005 | Riehl et al. |
| 2006/0047316 | A1 | 3/2006 | Fischell et al. |
| 2006/0069403 | A1* | 3/2006 | Shalon ................... A61B 90/02 606/192 |
| 2006/0205993 | A1 | 9/2006 | Fischell et al. |
| 2006/0224216 | A1 | 10/2006 | Pless et al. |
| 2007/0142886 | A1 | 6/2007 | Fischell et al. |
| 2007/0179558 | A1 | 8/2007 | Gliner et al. |
| 2007/0255322 | A1 | 11/2007 | Gerber et al. |
| 2007/0287931 | A1* | 12/2007 | Dilorenzo .......... A61K 31/5513 600/545 |
| 2008/0046026 | A1 | 2/2008 | Pless et al. |
| 2008/0051638 | A1 | 2/2008 | Iliff |
| 2008/0058664 | A1 | 3/2008 | Mirro |
| 2010/0210894 | A1 | 8/2010 | Pascual-Leone et al. |
| 2010/0228075 | A1 | 9/2010 | Lu |
| 2011/0213194 | A1 | 9/2011 | Fischell et al. |
| 2013/0137918 | A1 | 5/2013 | Phillips et al. |
| 2017/0021188 | A1 | 1/2017 | Lu |
| 2019/0224490 | A1 | 7/2019 | Goadsby et al. |

FOREIGN PATENT DOCUMENTS

| | | |
|---|---|---|
| WO | WO-2010102221 A1 | 9/2010 |
| WO | WO-2016090333 A1 | 6/2016 |

OTHER PUBLICATIONS

Anatomy of a Migraine: The Phases of a Migraine Attack and Their Symptoms—Part 2: The Headache and Postdrome [webpage], retrieved from the Internet:< http://headaches.about.corn/cs/headpain101/a/anatonny_mig_2.htm>, updated Jan. 9, 2008, 2 pages total.
EESR for EP1565084 dated Jun. 8, 2018.
European search report and search opinion dated Mar. 29, 2017 for EP Application No. 10749401.5.
International search report and written opinion dated Feb. 11, 2016 for PCT Application No. PCT/US2015/064128.
International Search Report and Written Opinion of PCT Application No. PCT/US2010/026383, mailed May 13, 2010, 10 pages total.
Lipton, et al. Single-pulse transcranial magnetic stimulation for acute treatment of migraine with aura: a randomised, double-blind, parallel-group, sham-controlled trial. Lancet Neurol. Apr. 2010;9(4):373-80. doi: 10.1016/S1474-4422(10)70054-5. Epub Mar. 4, 2010.
Notice of allowance dated Jul. 5, 2016 for U.S. Appl. No. 12/718,163.
"Office action dated Feb. 13, 2018 for U.S. Appl. No. 14/959,275."
Office action dated Mar. 6, 2015 for U.S. Appl. No. 12/718,163.
Office action dated Jun. 6, 2017 for U.S. Appl. No. 15/285,249.
Office action dated Jun. 21, 2013 for U.S. Appl. No. 12/718,163.
Office action dated Jul. 24, 2014 for U.S. Appl. No. 12/718,163.
Office action dated Aug. 30, 2012 for U.S. Appl. No. 12/718,163.
Office action dated Sep. 19, 2017 for U.S. Appl. No. 14/959,275.
U.S. Appl. No. 14/959,275 Office Action dated Nov. 2, 2018.
U.S. Appl. No. 15/831,795 Office Action dated Jan. 2, 2019.
U.S. Appl. No. 15/831,795 Office Action dated Jul. 25, 2019.
U.S. Appl. No. 16/270,465 Office Action dated Feb. 19, 2020.
U.S. Appl. No. 16/270,465 Office Action dated Mar. 12, 2019.
U.S. Appl. No. 16/270,465 Office Action dated May 14, 2019.
U.S. Appl. No. 16/270,465 Office Action dated Sep. 9, 2019.
European Communication pursuant to Article 94(3) EPC dated Feb. 7, 2021, of counterpart European Application No. 10 749 401.5.

* cited by examiner

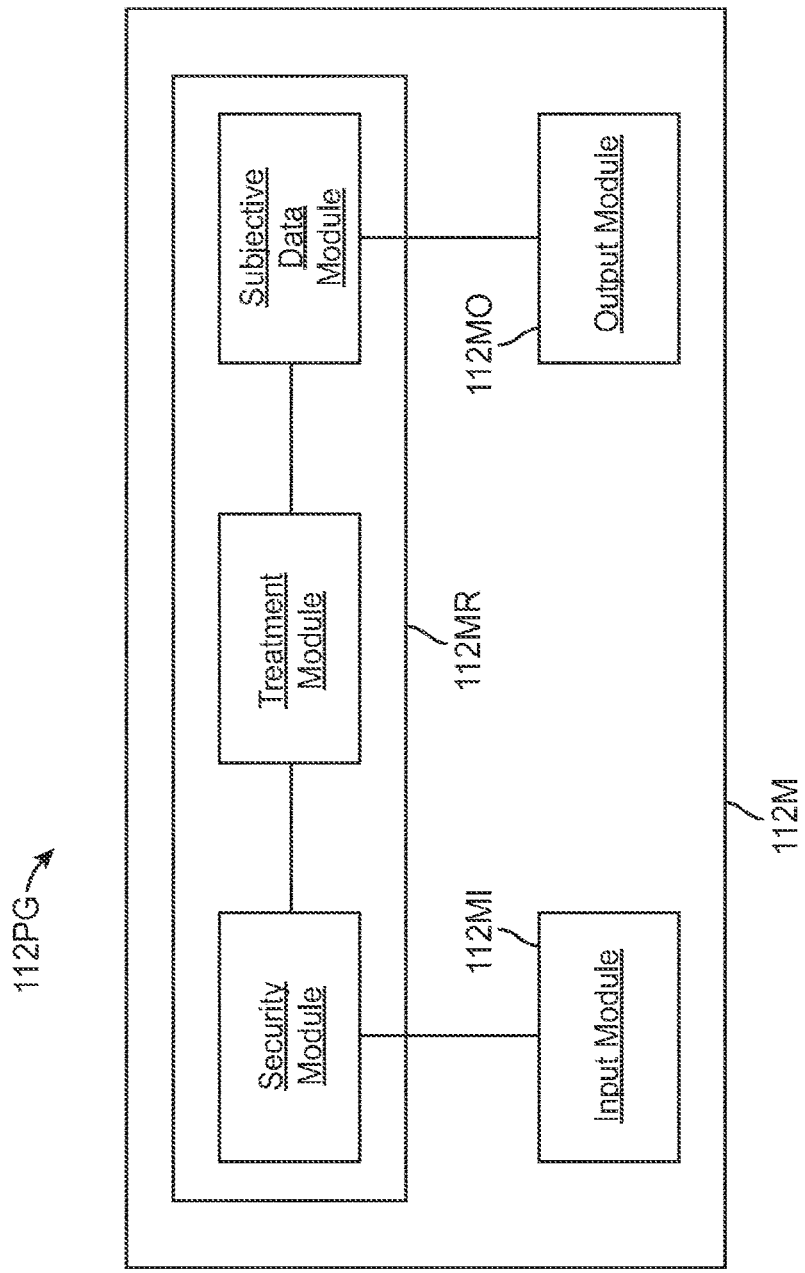
FIG. 1C1

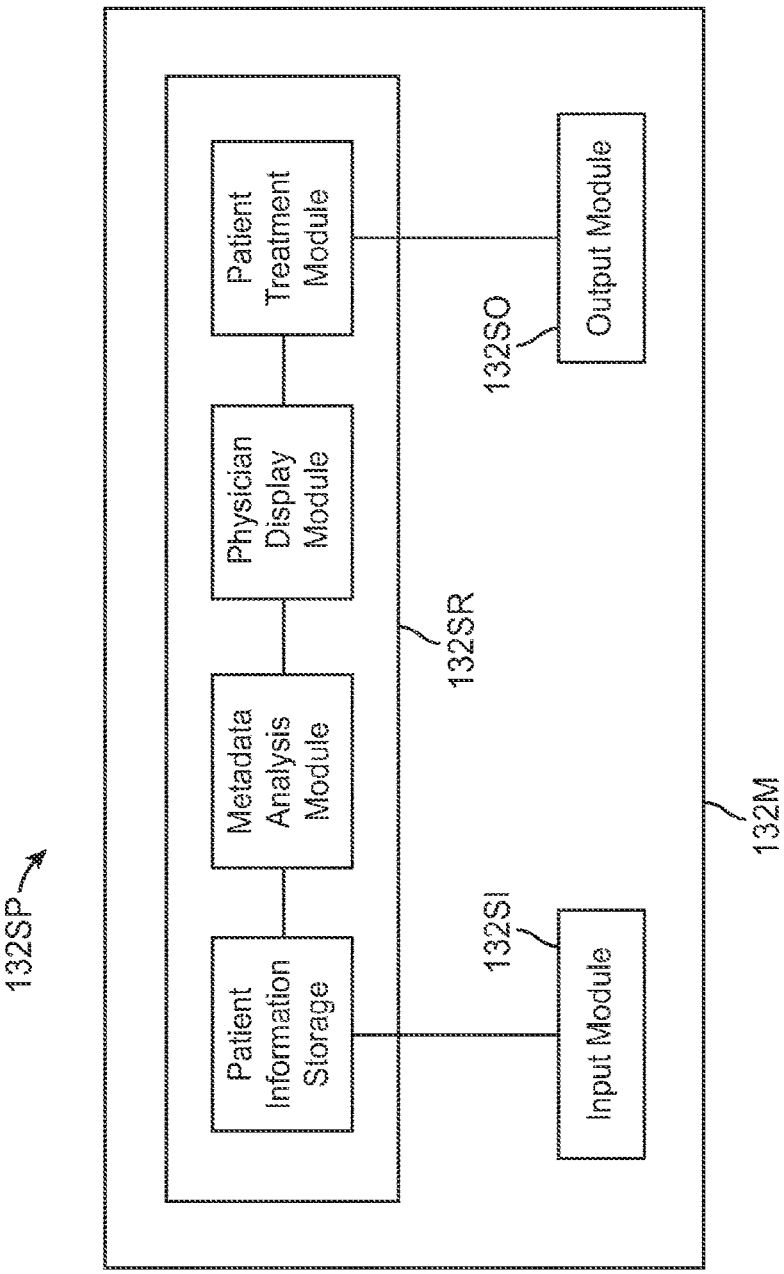
FIG. 1D1

Menu  My Profile  My Devices  TMS Service  Treatment History/Journal  Documents/Tutorials  Logout

*Treatment History & Headache Diary*

| List View | Episode Symptoms & Medications | Headache Diary | | | | | | |
|---|---|---|---|---|---|---|---|---|
| Date | Time | Type | Edit | | Assessment At | Pain Level | Sensitivity to Light | Sensitivity to Sound | Nausea Level |
| 9/20/2008 | 9:45am | Headache Diary | ✚ ✎ ✗ | 24 hours | 0 | | 0 | 0 |
| 9/20/2008 | 9:45am | Headache Diary | ✚ ✎ ✗ | 12 hours | 1 | 2 | 1 | 0 |
| 9/20/2008 | 9:45am | Headache Diary | ✚ ✎ ✗ | 2 hours | 3 | 2 | 2 | 0 |
| 9/20/2008 | 10:20am | *Treatment* | ✚ ✎ | | | | | |
| 9/20/2008 | 9:45am | Headache Diary | ✚ ✎ ✗ | 12 hours | 3 | 3 | 1 | 0 |
| 9/20/2008 | 10:20am | *Treatment* | ✚ ✎ | | | | | |
| 9/20/2008 | 9:45am | Headache Diary | ✚ ✎ ✗ | 6 hours | 3 | 3 | 2 | 0 |
| 9/20/2008 | 10:20am | *Treatment* | ✚ ✎ | | | | | |

FIG. 2G

- 305 — PRESENT MENU W/DIARY AND TX. OPTIONS
- 310 — TREAT PATIENT & TIME STAMP
- 315 — ENTER SUBJECTIVE PT. DATA
  - 315A — PRESENT PAIN LEVELS
  - 315B — PRESENT PHOTOPHOBIA LEVELS
  - 315C — PRESENT PHONOPHOBIA LEVELS
  - 315D — PRESENT NAUSIA LEVELS
- 320 — TIME STAMP SUBJECTIVE PT. DATA
- 325 — PRESENT OPTION TO ENTER SUBJECTIVE PT. DATA AGAIN LATER
- 330 — ENTER SUBJECTIVE PT. DATA SECOND TIME
- 335 — TIME STAMP W/SECOND TIME
- 340 — CONNECT TX. DEVICE TO PT. COMPUTER
- 345 — LOG PT. ONTO WEBSITE
- 350 — UPLOAD TX. DEVICE DATA TO SERVER
- 355 — PT. REVIEW AND ANNOTATE DATA
- 360 — PHYSICIAN REVIEW PT. DATA
- 365 — PHYSICIAN COMPARE PT. DATA W/META DATA
- 370 — PHYS. DETERMINE TX. PARAMETERS
- 375 — WRITE TX. TO PIM
- 380 — TRANSPORT PIM TO PT. DEVICE
- 385 — INSERT PIM INTO PT. DEVICE
- 390 — TREAT PT. IN RESPONSE TO TX PARAMETERS
- 395 — REPEAT

FIG. 3

PROPHYLACTIC TREATMENT FOR MIGRAINE HEADACHES

CROSS-REFERENCES TO RELATED APPLICATIONS

The present application is a continuation of U.S. patent application Ser. No. 15/831,795, filed Dec. 5, 2017, which is a continuation of U.S. patent application Ser. No. 15/285,249filed Oct. 4, 2016, which is a continuation of U.S. patent application Ser. No. 12/718,163, filed Mar. 5, 2010, now U.S. Pat. No. 9,492,680, which claims the benefit under 35 USC 119(e) of U.S. Provisional Application No. 61/158,087filed Mar. 6, 2009; the full disclosures of which are incorporated herein by reference in its entirety.

The subject matter of the following patents and applications may be relevant to the present application: U.S. Pat. Nos. 6,402,678; 7,294,101; Ser. No. 10/327,163 published as 2004/0122281; Ser. No. 10/929,586 published as 2006/0047316; Ser. No. 11/305,276 published as 2007/0142886; Ser. No. 11/436,676 published as 2006/0205993; the full disclosures of which are incorporated herein by reference.

BACKGROUND OF THE INVENTION

1. Field of the Invention

The present invention is relates to the diagnosis and treatment of neurological disorders, for example migraine episodes. Although embodiments make specific reference to the treatment and diagnosis of migraine episodes (hereinafter "migraines") with magnetic fields, embodiments of the present invention will have application to the diagnosis and treatment of many neurological disorders, for example depression, Parkinson's' disease, stroke, chronic pain, tinnitus and epilepsy Many people suffer from migraine episodes. Migraine episodes can be debilitating and can affect patient quality of life and productivity. The migraine episode can debilitate a person, may last for up to seventy two hours, and may require medical attention in at least some instances. Although many people associate migraine episodes with headaches, a migraine episode can include four phases: a prodrome phase, also referred to as "pre-headache"; an aura phase; a headache phase; and postdrome phase. At least some people with migraines experience the prodrome phase. When present, the prodrome phase occurs prior to the migraine headache phase. The prodrome phase may be experienced for hours or even days before the migraine headache phase, and may include symptoms such as altered mood, irritability, depression or euphoria, fatigue, yawning, excessive sleepiness, craving for certain food, stiff muscles, constipation or diarrhea, increased urination, and other visceral symptoms. At least some people with migraines can experience the aura phase, which can occur after the prodrome phase and before the headache phase. The aura phase may include visual symptoms and non-visual symptoms. The visual symptoms may include flashes of lights or formations of dazzling lines, blurred or shimmering or cloudy vision, and tunnel vision. The non-visual symptoms of the aura phase may include auditory and/or olfactory hallucinations, temporary dysphasia, vertigo, tingling or numbness of the face and extremities, and hypersensitivity to touch. The headache phase can include one or more of many symptoms, for example pain, photophobia, phonophobia, olfactophobia, blurred vision, nasal stuffiness, diarrhea, polyuria, pallor, sweating, localized edema of the scalp or face, scalp tenderness, and stiffness and tenderness of the neck, in at least some instances. The postdrome phase can last for hours, in some instances days, and symptoms may include one or more of fatigue, poor concentration, poor comprehension, and lowered intellect level in at least some instances. Due to the painful and debilitating nature of migraine episodes that occur in at least some instances, effective treatments are currently sought.

One approach for treating migraines can be for the patient to keep a diary to determine migraine triggers, for example a handwritten diary notebook, such that the patient may be able to prevent migraines by avoiding migraine triggers in at least some instances. Although hand written diary entries can be useful to determine migraine triggers, in at least some instances interpretation of hand written diary entries can be difficult and/or time consuming. Further, hand written entries are prone to error, which can be further complicated in at least some instances when the patient suffers from a debilitating neurological condition, such as a migraine episode, and chooses to record their symptoms after the headache episode completes, thus affecting the accuracy and completeness of the records. In at least some instances, diary entries can also be difficult for a physician to compare among patients so as to determine the effectiveness treatment. Therefore, although information from diaries may be helpful, the information can be inaccurate and difficult to interpret in at least some instances.

Another approach to the treatment of migraines is for the patient to take medication. Although medications can be at least partially effective in some instances, patients may still suffer migraine episodes when taking migraine medication, such that the medication may be only partially effective. Also, at least some medications can potentially result in side effects for the patient and may lose effectiveness over time, such that migraine treatment with medication can be less than ideal in at least some instances.

Another approach to migraine treatment can be to employ a portable magnetic pulse system, in which the system can deliver a short duration magnetic pulse onto the patient's brain. Although such systems can be effective in treating migraines, work in relation to embodiments of the present invention suggests that at least some of these magnetic pulse systems may not be utilized as effectively as would be ideal on an individual bases, due at least in part to difficulty in determining the ideal exposure to pulses for treating migraines.

Therefore, a need exists for improved methods and apparatus for treatment of neurological conditions such migraines. Ideally, such improved methods and apparatus will overcome at least some of the above mentioned problems associated with current methods and apparatus for treating neurological conditions such as migraines.

2. Description of the Background Art

Published Patent Applications and Patents that may be relevant to aspects of the present application include: 2001/0051819; 2001/0056290; 2002/0002390; 2003/0028072; 2003/0088290; 2003/0120324; 2004/0153129; 2004/0181115; 2004/0249422; 2006/0047316; 2006/0205993; 2006/0224216; U.S. Pat. Nos. 6,402,678; 7,223,234; and 7,294,101.

SUMMARY OF THE INVENTION

The present invention relates to the diagnosis and treatment of neurological disorders, for example migraine episodes. Although embodiments make specific reference to the treatment and diagnosis of migraine episodes with magnetic fields, embodiments of the present invention will have application to the diagnosis and treatment of many neurological disorders, for example depression, Parkinson's' disease, stroke, chronic pain, tinnitus and epilepsy. A treatment apparatus, for example a treatment device, may comprise circuitry to treat a neurological disorder of the patient, for example circuitry configured to generate a magnetic field to treat migraines. The treatment apparatus may comprise a patient interface, for example a touch screen display, in which the patient interface is configured for the patient to enter subjective patient data for an assessment of his or her subjective sensations, for example pain and other symptoms associated with migraines. The patient treatment apparatus comprising a patient interface configured for the patient to enter his or her own subjective patient data can result in more accurate recording of the subjective patient data and treatment data, such that a treating physician can more accurately diagnose and treat the patient having the neurological disorder. For example, this treatment apparatus can ensure that the patient enters his or her subjective patient data near the time of treatment because the patient can use the treatment device to enter the subjective patient data. Also, the treatment parameters can be accurately recorded with the subjective patient data as the treatment apparatus can also be used to record the time and date of the delivery of each treatment and, if appropriate, treatment parameters such as dose or magnitude. In many embodiments, the treating physician can view data for the patient to diagnose the patient, and the physician can treat the patient in response to the diagnosis with a treatment plan. For example, the treatment device may be configured to permit patient treatment only when a patient specific module is inserted into the treatment device, in which the patient specific module includes instructions for treatment according to the treatment plan so as to ensure that the treatment device is used in accordance with the treatment plan determined by the physician.

In a first aspect, embodiments of the present invention provide an apparatus to treat a neurological disorder of a patient. The apparatus may comprise a patient treatment device. Circuitry is configured to generate a magnetic field to treat the neurological disorder. At least one processor comprising a tangible medium is coupled to the circuitry to control treatment of the patient. A patient interface is coupled to the at least one processor and configured for the patient to enter patient data for a plurality of subjective patient sensations related to the neurological disorder.

In many embodiments, the at least one processor is configured to store the treatment data and the entered patient data.

In many embodiments, the plurality of subjective patient sensations comprises a least one of a plurality of patient symptoms, for example migraine symptoms, or a plurality of patient triggers, for example migraine triggers.

In many embodiments, the at least one processor and the patient interface are configured for the patient to enter the plurality of subjective patient sensations at each of a plurality of patient data entry times. The plurality of subjective patient sensations may comprise subjective patient sensations, and the subjective patient sensations may comprise at least one of a pain, a sensitivity to light, a sensitivity to sound, a nausea, an aura or a neck stiffness.

In many embodiments, the plurality of subjective patient sensations comprises a first plurality of subjective patient sensations corresponding to a first time and a second plurality of subjective patient sensations corresponding to a second time. The first plurality of subjective patient sensations may comprise at least one of a first pain level, a first sensitivity to light level, a first sensitivity to sound level, a first nausea level a first aura level or a first neck stiffness level, and the second plurality of subjective patient sensations may comprise at least one of a second pain level, a second sensitivity to light level, a second sensitivity to sound level, a second nausea level, a second aura level or a second neck stiffness level. For example, the first plurality of subjective patient sensations may comprise the first pain level and the second plurality of subjective patient sensations may comprise the second pain level.

In many embodiments, the patient interface comprises a touch screen display coupled to the at least one processor for the patient to enter the plurality of subjective patient sensations in response to a plurality of selectable icons shown on the display for each sensation so as to determine a level the sensation. For example, the at least one processor may be configured to show on the display sequentially a first plurality of selectable icons for a first sensation and a second plurality of selectable icons for a second sensation.

In many embodiments, the at least one processor and the patient interface are configured for the patient to select one level from among a plurality of patient levels for each sensation, and the at least one processor is configured to record the one level for each sensation.

In many embodiments, the at least one processor comprises a non-volatile memory configured to record the plurality of subjective patient sensations in response to input from the patient and to record a treatment time for each treatment with the magnetic field. A clock can be configured to record a treatment time when the patient is treated and an entry time when the patient enters the plurality of subjective patient sensations. The at least one processor can be configured to time stamp the patient data with a first time stamp at a first time corresponding to a first plurality of subjective patient sensations and configured to time stamp the patient data with a second time stamp at a second time corresponding to a second plurality of subjective patient sensations. The patient interface can be configured for the patient to select the second time and the interface may comprise an alarm coupled to a timer to alert the patient when the second time occurs.

In many embodiments, a casing is configured to enclose the at least one processor and the circuitry such that the patient interface is visible to the patient for data entry, and the circuitry comprises a coil to generate the magnetic field near at least one of a head or a neck of the patient. The casing, the circuitry, and the patient interface are configured for the patient to lift the casing, the circuitry and the at least one processor to position the coil near the at least one of the head or the neck for treatment.

In many embodiments, a patient specific module is configured to couple to the at least one processor and the circuitry to permit treatment of the patient. For example, the at least one processor and the patient specific module can be configured to permit treatment and only when the patient specific module is inserted into a unique and specific treatment device. The patient specific module may comprise parameters to control the treatment, such that the treatment may be customized to the patient based on the treatment plan determined by the physician.

The patient specific module may be configured in many ways to permit, and optionally control, the patient treatment. For example, the patient specific module may comprise a second tangible medium configured to store a unique identifier, such as at least one of a patient identity, and instructions to treat the patient. The patient specific module may also comprise a second processor coupled to the second tangible medium. The patient specific module can be configured for insertion into a receptacle of the treatment device, which receptacle is coupled to the at least one processor so as to couple the second tangible medium to the at least one processor. Alternatively or in combination, the patient specific module may comprise a software module embodied in the tangible medium of the treatment device, and the information stored on the patient specific module may be loaded into a specific treatment device with at least one of a secure internet connection, a telephone connection or a cellular connection.

The instructions to treat the patient can be configured in response to input from a physician who provides care for the patient. The instructions to treat the patient may be configured to customize each treatment with at least one of a pulse width, a pulse peak or a number of pulses, and the instructions may be stored on the second tangible medium in response to the input from the physician.

The instructions to treat the patient may include a number of available treatments stored on the second tangible medium, and the at least one processor can be configured to decrease the number of available treatments stored on the second tangible medium each time the patient is treated. The instructions to treat the patient may be configured to allow no more than a maximum number of pulses over a period of time.

In another aspect, embodiments of the present invention provide a system to treat a patient for a neurological disorder. The system comprises a patient treatment device and a server. The patient treatment comprises at least one processor comprising a tangible medium, and a patient interface. The patient interface is coupled to the at least one processor and configured to receive patient data input by the patient for a plurality of subjective patient sensations related to the neurological disorder. The server comprises a processor system comprising a server tangible medium. The at least one processor is configured to upload to the server the patient data for the plurality of subjective patient sensations related to the neurological disorder.

In many embodiments, the at least one patient treatment device further comprises circuitry configured to generate a magnetic field to treat the neurological disorder. The at least one processor is coupled to the circuitry to control treatment of the patient and to record data from the treatment of the patient and store the data in a non-volatile memory. The at least one processor is configured to store the plurality of subjective patient sensations in the non-volatile memory. The processor system further comprises a patient processor comprising a tangible medium locatable near the patient. A physician processor is coupled to the server to receive patient data. The physician processor comprises a physician display for the physician to view the patient data for the plurality of subjective patient sensations. The patient processor is configured to couple to the non-volatile memory and upload the treatment data and subjective patient sensations to the server when the treatment device is coupled to the patient processor.

In many embodiments, the patient processor comprises a display for the patient to view the patient data, and the patient processor is configured for the patient to edit the patient data.

In many embodiments, the server comprises a statistical compilation of patient meta data from a plurality of patients for the physician to compare with the patient data for the plurality of subjective patient sensations to determine the treatment of the patient.

In many embodiments, a write module is configured to couple to a patient specific module and coupled to the physician processor, and the physician processor is configured to identify and transmit patient data to the write module. The write module can be configured to write instructions for patient treatment to the patient specific module in response to treatment commands input from the physician, and the patient specific module can be configured to control the treatment with the instructions.

In another aspect, embodiments of the present invention provide a method of treating a neurological disorder of a patient. A magnetic field is generated with circuitry to treat the neurological disorder. Patient data are entered for a plurality of subjective patient sensations related to the neurological disorder. The patient enters the subjective patient data, and the magnetic field is generated in response to the patient data.

In many embodiments, the plurality of subjective patient sensations comprises a first plurality of subjective patient sensations corresponding to a first time and a second plurality of subjective patient sensations corresponding to a second time. The first time may be separated from the second time by at least about 15 minutes. The first plurality of subjective patient sensations may comprise at least one of a first pain level, a first sensitivity to light level, a first sensitivity to sound level, a first nausea level a first aura level or a first neck stiffness level, and the second plurality of subjective patient sensations may comprise at least one of a second pain level, a second sensitivity to light level, a second sensitivity to sound level, a second nausea level, a second aura level or a second neck stiffness level.

BRIEF DESCRIPTION OF THE DRAWINGS

FIG. 1C1 shows a computer program embodied on a tangible medium comprising instructions to permit and control treatment of the patient with the at least one processor of FIGS. 1A and 1B;

FIG. 1D1 shows a program of the system for treating patients as in FIGS. 1A-1C;

FIG. 2G shows the treatment history and journal information shown on a display of a processor system as in FIG. 1D for review by at least one of the patient or the physician; and FIG. 3 shows a method of treating a patient for a neurological disorder with system as in FIGS. 1A to 2G, in accordance with embodiments of the present invention.

DETAILED DESCRIPTION OF THE INVENTION

Figure 1A:
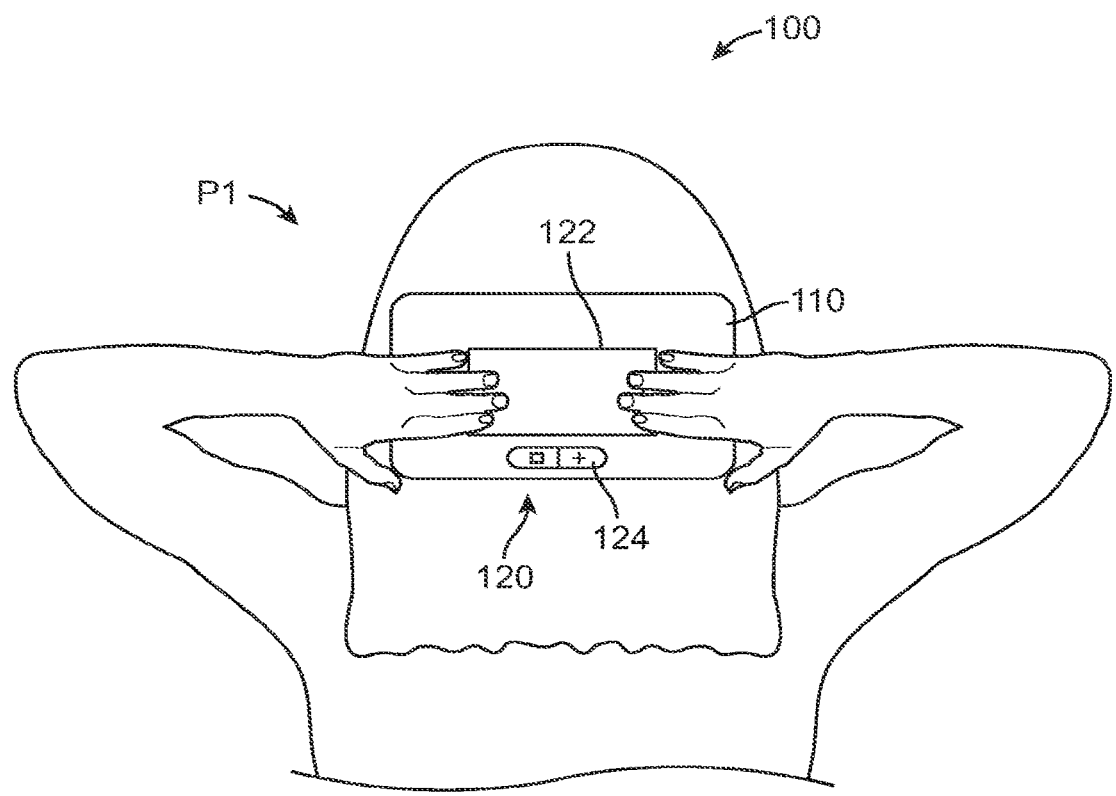
FIG. 1A shows a patient treating herself for a neurological disorder with a hand held treatment device, in accordance with embodiments of the present invention.

The present invention is related to the diagnosis and treatment of neurological disorders. Although specific embodiments make reference to the treatment and diagnosis of migraine headaches with magnetic fields, embodiments of the present invention will have application to the diagnosis and treatment of many neurological disorders, for example epilepsy.

As used herein, a symptom encompasses any indication of disease noticed or felt subjectively by a patient. With respect to migraines, symptoms may include at least one of pain, a sensitivity to light, a sensitivity to sound, nausea, aura, or neck stiffness. For example, the symptom may comprise sensitivity to light, also referred to as photophobia. The symptom may comprise a symptom of a pre-headache phase of migraine, for example neck stiffness.

The systems, apparatus, methods and devices described herein may utilize a treatment apparatus configured to collect treatment information coupled to a patient interface, for example a touch screen display, configured for the patient to enter an assessment of his or her subjective sensations, for example pain symptoms associated with migraines. This coupling of the treatment apparatus to the patient interface can result in more accurate recording of the patient sensations and treatment, such that a treating physician can more accurately diagnose and treat the patient. The coupling of the treatment apparatus to the patient interface can ensure that the patient enters subjective sensation information near the time of treatment, and that the treatment parameters can be accurately recorded with the subjective sensation information because the same apparatus can be used to treat the patient and record the subjective sensation information. Also, because the patient has the treatment device readily available for treatment, the patient has the user interface readily available to enter the subjective patient information, which can ensure that the subjective patient information is actually entered due to ease of use and proximity to the treatment device. The subjective patient sensations may comprise at least one of a patient symptom of the neurological condition or a patient trigger of the neurological condition. For example the subjective patient sensations may comprise symptoms that correspond to migraine such as aura symptoms. Also, the subjective patient sensations may comprise triggers, for example environmental triggers, that may trigger migraine episodes. The treatment apparatus may additionally remind patients to enter subjective information at later time points if requested by the patient or physician to record the time course of response to treatment. The treatment apparatus records the time and date of treatments and the time and date of patient entered subjective information. This data may be uploaded to a private patient page on a server. The patient data may be further edited and annotated by the patient. In many embodiments, the patient's private physician may review the patient specific treatment and subjective data. Additionally, the physician may review meta-data analyses. In many embodiments, the treating physician can view data for the patient via the server, and diagnose and treat the patient with a treatment plan. The treating physician may enter this treatment plan to the server. Some of the instructions may be recommendations to the patient. Other treatment plan instructions may comprise changes to the instructions sent to the treatment apparatus. The server writes this portion of the treatment plan to a storage device, for example treatment instructions written to a smart card, thereby allowing a greater or lesser number of treatments over a specific time period, which storage device can be delivered to the treatment apparatus such that the patient can treat himself or herself in response to the physician's treatment plan.

Embodiments of the present invention can be used to diagnose and treat the patient, for example to determine the effectiveness of treatment such that the treating physician can readily modify the treatment. The patient can be given a forced choice selection to enter the subjective patient data, for example a graded forced choice selection, e.g. "none", "mild", "moderate", or "severe", for one of the subjective sensations, such that the data can be readily analyzed by the treating physician. Each physician can review the data from the treated patient and his or her other patients to diagnose and treat the patient. In addition to data from the treated patient and his or her other patients, the treating physician can also view data from other patients such that the data can be compared, for example with metadata. Therefore, physicians can evaluate the effectiveness of treatment from many treating physicians without violating patient confidentiality requirements, for example Health Insurance Portability and Accountability Act (hereinafter "HIPAA") requirements.

The treating physician can use the patient data to customize the treatment for the patient, for example with a treatment plan from the physician. For example, the physician may write treatment instructions to the server such that the appropriate tangible medium, for example a smart card, that can be given to the patient for use with the treatment device. The physician is able to evaluate the success of the treatment based on the patient data, and the treatment can be further customized by the physician, as he or she deems appropriate based on medical judgment. Therefore, the physician can iteratively diagnose and cause smart cards to be provided to the patient with customized treatment plans so as to optimize the treatment of the patient.

Embodiments of the present invention comprise at least one a prescription or a subscription to use the patient treatment device to ensure that the patient is treated in accordance with a physician treatment plan. The treatment device may be configured with a limited time and/or a limited number of treatments per the medical providers orders, and such that the prescription and/or subscription may be purchased by a third party. The treatment device can be programmed in accordance with the subscription and treatment plan in many ways. For example, the treatment device may be controlled with at least one of a digital subscription key installed via an encryption code, an electrical key such as a USB memory stick or a consumable key which must be physically installed on the device, such that the key provides a limited amount of treatment. The limited amount of treatment may comprise a limited number of treatments or a limited time over which treatment is available.

FIG. 1A shows a first patient P1 treating herself for a neurological disorder, for example a migraine, with a hand held treatment device 110. Hand held treatment device may comprise a component of a treatment system 100. For treatment, the patient can place treatment device 110 near the back of the head and neck. The treatment device 110 generates a magnetic field to treat the patient. Treatment device 110 includes a patient interface 120. Patient interface 120 comprises a display 122 and at least one button 124. Display 122 may comprise a touch screen display. At least one button 124 may comprise a plurality of buttons.

Figure 1B:
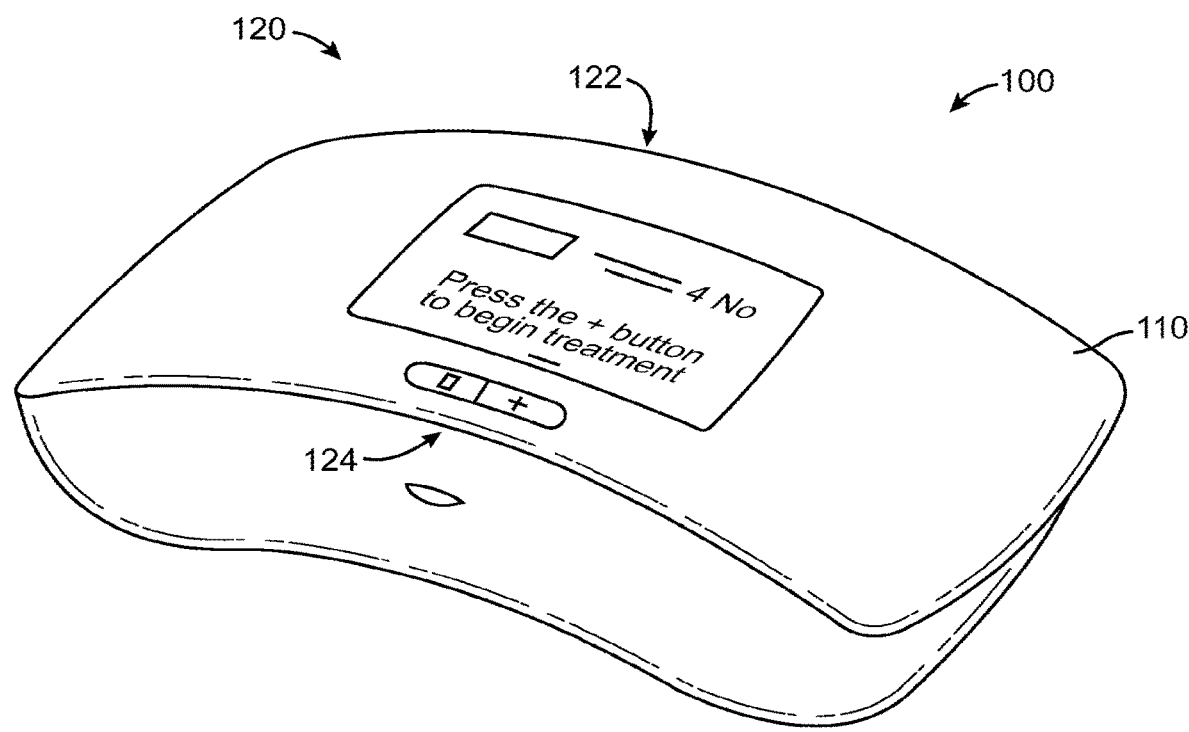
FIG. 1B shows the user interface of the hand held treatment device as in FIG. 1A.

FIG. 1B shows hand held treatment device 110 and patient interface 120 as in FIG. 1A. Display 120 may comprise instructions for the patient, for example "Press the + button to begin treatment". The display can show menus for the patient to select treatment or entry of patient data, for example data to measure a plurality of subjective patient sensations. Although the display shown may comprise a curved surface with a centrally located display, many configurations of the handheld treatment device 110 can be used. For example, the surface with the display may be flat, and the other surfaces curved. Alternatively or in combination, the treatment device may comprise a substantially rectangular geometry with many flat surfaces and corners with right angles.

Figure 1C:
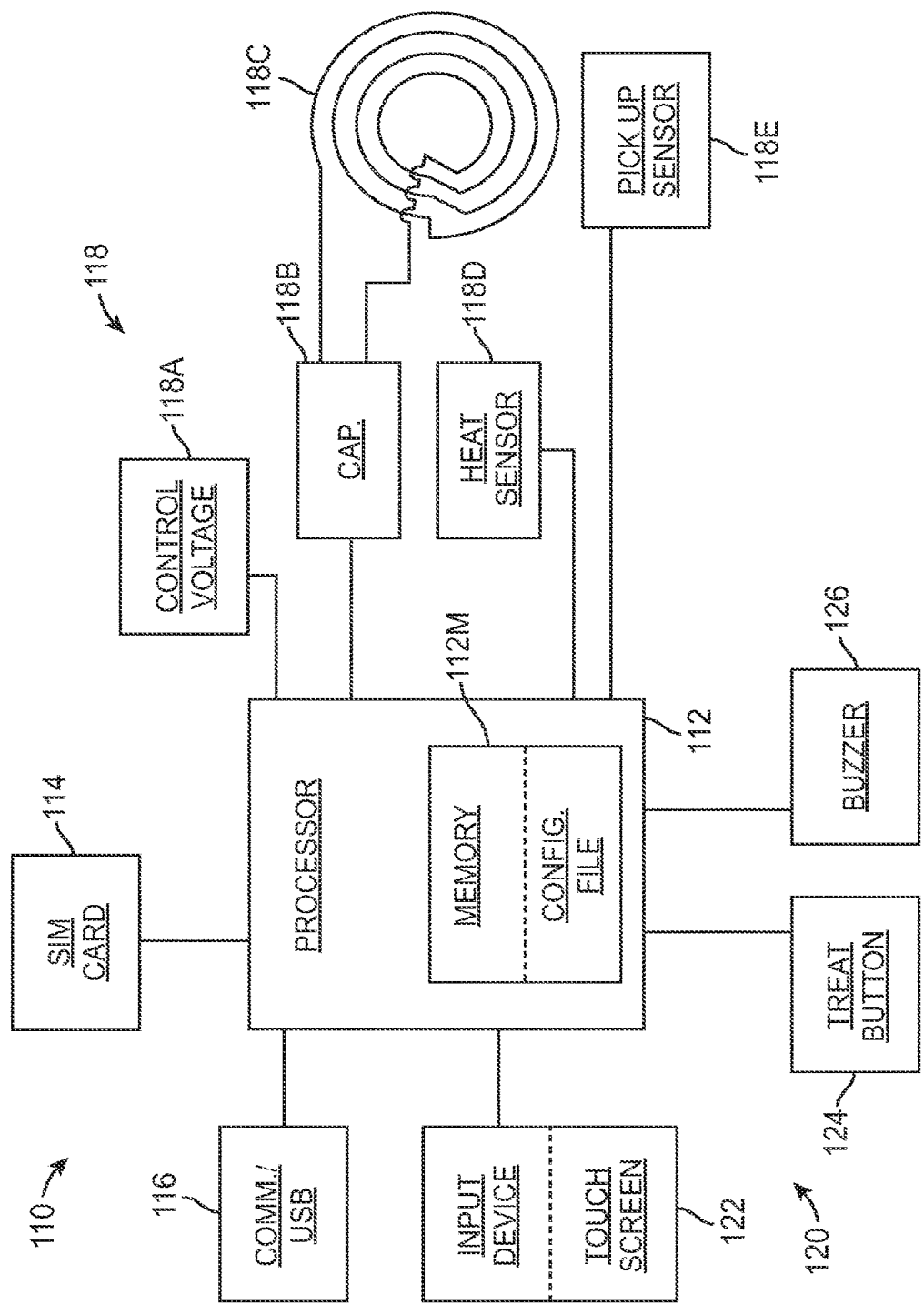
FIG. 1C shows a schematic illustration of the components of the hand held treatment device as in FIGS. 1A and 1B.

FIG. 1C shows a schematic illustration of the components of the hand held treatment device 110 as in FIGS. 1A and 1B. Many components of hand held treatment device 110 can be similar to components described in Pub. No. US 2006/0047316, the full disclosure of which has been previously incorporated by reference and which application includes subject matter that may be suitable for combination with the teachings described herein in accordance with some embodiments of the present invention. Patient treatment device 110 comprises a processor 112, which may comprise one or more processors, for example a distributed processor system. Processor 112 comprises a tangible medium such as a memory 112M. The memory may comprise volatile memory such as random access memory and non-volatile memory such as flash RAM. The memory 112M of processor 112 may comprise a configuration file, or "config." file, that includes parameters for the system to operate and deliver treatment to the patient, for example calibration and control voltage parameters. The processor 112 can be coupled to many additional components of the treatment device. The processor 112 comprises at least one processor, for example a single processor with instructions for treatment, and may comprise an additional processor, for example a display processor coupled to a touch screen display to control the acquisition of data from the patient.

Processor 112 can be coupled to a patient specific module (hereinafter "PSM"), for example a known subscriber identity module (hereinafter "SIM"). The PSM may also comprise a known smart card with patient treatment information. For example SIM 114 may comprise a smart card configured to control at least some aspects of the patient treatment, for example the number of pulses available for the patient over a specific time period. SIM 114 may comprise additional treatment parameters such as the maximum number of pulses per unit time that the patient can deliver. SIM 114 may also comprise instructions for a treatment plan, for example treatment commands. Processor 112 can be configured to reduce the number of treatments available for patient P1 that are stored on SIM 114 in response to delivery of a treatment to the patient. Processor 112 may comprise instructions to treat the patient in response to parameters stored on the SIM 114, for example the number of treatments. The SIM 114 may comprise a card that is inserted into the treatment device. SIM 114 may comprise a number keyed to the treatment device. For example, patient treatment device 110 may comprise a serial number written to non-volatile memory and SIM 114 can be keyed to the serial number.

The treatment parameters written to the SIM card may comprise a treatment plan. The treatment plan may comprise a maximum number of treatments over a period of time, for example no more than one treatment per hour. The treatment plan may also comprise a minimum number of treatments over the period of time, for example no less than one treatment per day. The treatment plan stored on the SIM card may also comprise instructions for prophylactic treatments, for example one treatment per day. The treatment device can be programmed to alert the patient for treatment. The treatment plan may also comprise a number of pulses to be delivered with a each treatment, for example two pulses per treatment. One of ordinary skill in the art, for example a treating physician, can determine an optimal treatment plan for a patient based on empirical studies with an empirical number patients, for example studies comprising meta data from about 100 patients treated by additional physicians.

Processor 112 can be coupled to a patient interface 120. The patient interface 120 may comprise many known interface components, for example known displays, touch screens, buttons and buzzers. An input device of interface 120 may comprise a touch screen 122. The input device may comprise many known input devices such as pointing devices, keyboards and touch screen 122. Patient interface 122 comprises a treat button 124 for the patient to initiate treatment. However, the treat button can provide additional input, for example for the patient to enter data. Patient interface 120 comprises an alarm, for example a buzzer 126, configured to alert the patient. Buzzer 126 can alert the patient when it is time for the patient to enter additional information into the patient journal. Buzzer 126 can also alert the patient that it is time for a treatment with the magnetic field.

Processor 112 can be coupled to circuitry 118 to treat the patient with the magnetic field. Circuitry 118 may comprise a coil 118C to generate the magnetic field to treat the patient. Circuitry 118 may comprise a control voltage 118A, capacitor 118B, one coil 118C, a heat sensor 118D and a pick up sensor 118E. Coil 118C can be coupled to a capacitor 118B. Capacitor 118B can be charged and the charge can be released to treat the patient. Capacitor may comprise a plurality of capacitors to store sufficient charge. Control voltage 118A can be used to set the voltage of the capacitor and charge the capacitor to the set voltage, for example with a voltage controller. Pick up sensor 118E can measure the magnetic field, for example the peak magnetic field, when capacitor 118B discharges through coil 118C. Circuitry 118 may comprise switches coupled to processor 112 to control the circuitry, for example charging and discharging of capacitor 118B. Heat sensor 118D can measure heat of capacitor 118D.

Processor 112 can be coupled to communication circuitry 116. Communication circuitry 116 may comprise a USB port on treatment device. Communication circuitry 116 may comprise wireless communication circuitry configured to communicate with a wireless communication protocol, for example a Bluetooth™ protocol. Communication circuitry 116 can upload patient data to a remote server where the patient data can be stored for review by a physician. Communication circuitry 116 can also download treatment related parameters, for example parameters for the configuration file. The treatment related parameters of the configuration file may be stored on SIM 114.

The patient specific module may comprise a processor, for example a processor of a smart card, such that the tangible medium of the smart card and the processor of the smart card comprise the at least one processor of the treatment device. The instructions for treatment can be embodied in tangible medium of the at least one processor, in which a computer program comprising instructions for patient treatment is embodied on the tangible medium.

FIG. 1C1 shows a computer program 112PG embodied on tangible medium 112M comprising instructions to permit and control treatment of the patient with the at least one processor of FIGS. 1A, 1B and 1C. Computer program 112PG comprises an input routine 112MI, and output routine 112MO and a run routine 112MR. Input routine 112MR may comprise an input module operatively coupled to a source of data, for example at least one of the treatment and patient data of the smart card or the subjective input data of the patient interface. Run routine 112MR may comprise, for example, a security module, a treatment module and a subjective data module to collect the subjective data from the patient. The security module may comprise instructions configured to process the patient specific identifier and the device identifier and encryption codes of the smart card. The treatment module may comprise instructions configured to determine the treatment parameters to the treatment circuitry in response the patient treatment parameters from the patient specific module and the configuration file. The subjective data module can be configured to ask questions of the patient as described above. Each of the security module, the treatment module and the subjective data module can be operatively coupled to the output module to output relevant information to the user and physician as appropriate. For example, the security module can indicate when the patient specific module is read correctly when inserted into the receptacle. The treatment module can output treatment parameters to the circuitry for treatment, and the subjective data module can output data to another computer such that the subjective data can be sent to the treating physician.

It should be appreciated that the specific modules and/or routines shown in FIG. 1C1 provide a particular configuration of the computer program 112PG, according to some embodiments of the present invention. The individual modules and/or routines illustrated in FIG. 1C1 may include multiple subroutines that may be performed in various sequences as appropriate to the individual module and/or routine. Furthermore, additional modules and/or routines may be added or removed depending on the particular applications. One of ordinary skill in the art would recognize many variations, modifications, and alternatives.

Figure 1D:
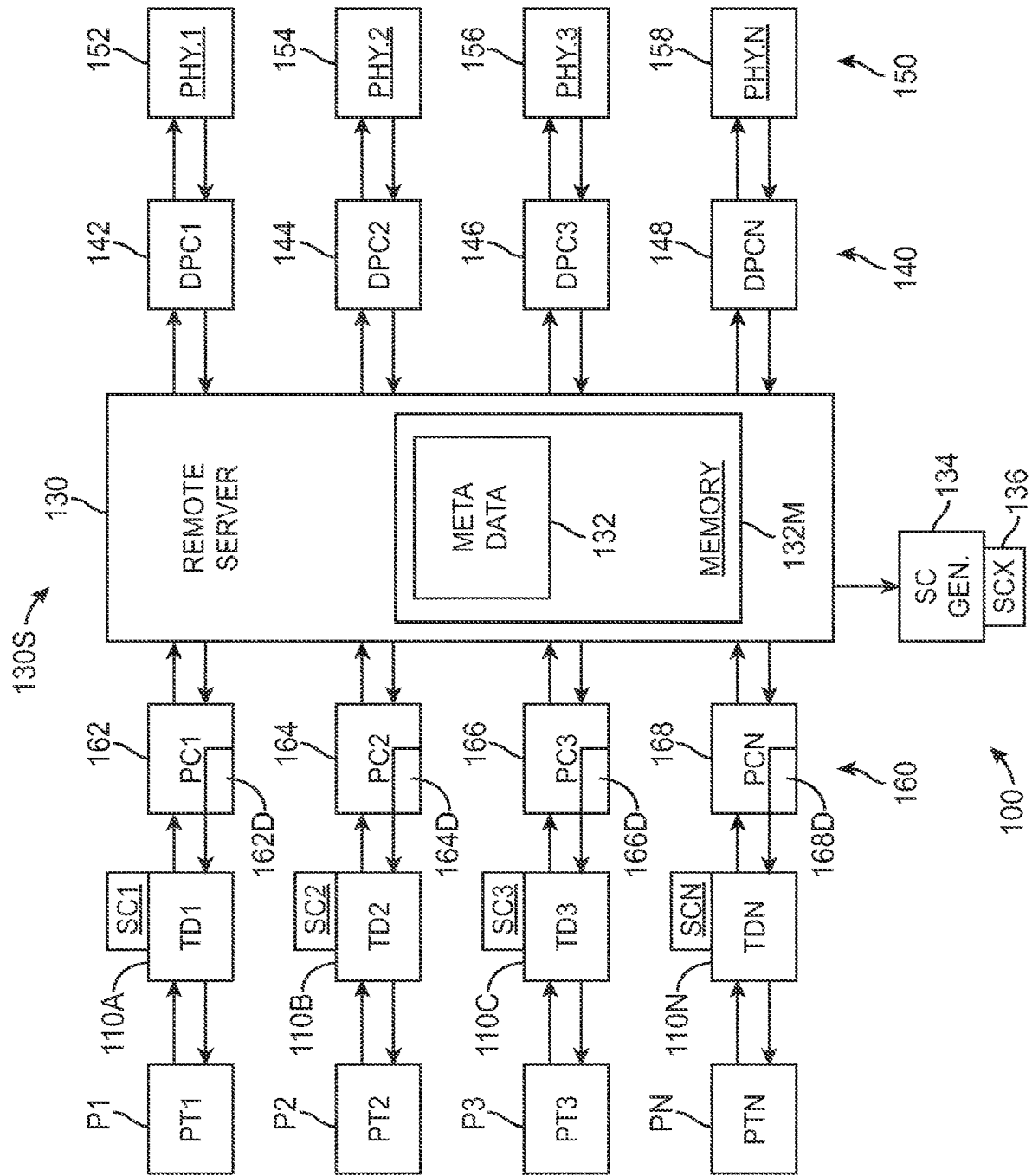
FIG. 1D shows a system for treating a plurality of patients with a plurality of devices as in FIGS. 1A-1C.

FIG. 1D shows a system 100 for treating a plurality of patients with a plurality of devices as in FIGS. 1A-1C. System 100 may comprise a plurality of patient treatment devices, a plurality of patient computers 160, a remote server 130, and a plurality of remote physician computers 140 for a plurality of physicians to view the patient data of his or her patients remotely. System 100 may comprise a processor system 130S to transmit patient data from the patient treatment devices to the physician computers and to write patient treatments onto the SIM cards. Processor system 130S may comprise the plurality of patient computers 160, the remote server 130, the physician computers 140. Processor system 130S comprises a tangible medium 132M. The tangible medium 132M of the processor system 132M may comprise a tangible medium of server 130, and the tangible media of the computers connected to the server, such that instructions and programs can be distributed among the processors of the processor system 130S. The processor system can be connected to a SIM card writer 134 to write patient treatments onto the SIM cards.

The components of processor system 130 can be coupled to each other in many known ways, for example over the Internet. Server 130 may comprise a processor coupled to the internet, for example configured as a website, and the patients and physicians may access the website with browsers on their respective computers. Server 130 can download software components to processors of processor system 130S, for example web browser plug in modules, that can be run on the computers of the physicians and patients.

The plurality of patients may comprise a first patient P1, a second patient P2, a third patient P3 and an Nth patient PN. Each of the patients has a corresponding patient treatment device (hereinafter "TD"), and each patient treatment device can be similar to patient treatment device 110, as described above. First patient P1 has a first patient treatment device 110A. Second patient P2 has a second patient treatment device 110B. Third patient P3 has a third patient treatment device 110C. Nth patient PN has an Nth patient treatment device 110N. Each of the treatment devices may comprise a unique treatment device identifier, for example a serial number, and each of the patients may have a unique patient identifier, such that each treatment device can be uniquely identified and uniquely paired with the patient assigned to the specific treatment device.

Each patient treatment device comprises a patient interface, as described above. Each patient can enter data into the patient treatment device, and view messages on a display as described above.

Each patient treatment device has a corresponding SIM card, in which each SIM card is keyed to the specific treatment device. The unique treatment device identifier, for example serial number, of each treatment device can correspond uniquely to each patient, so as to ensure that each patient receives the correct treatment. First treatment device 110A has a first SIM card SC1. Second treatment device 110B has a second SIM card SC2. Third treatment device 110C has a third SIM card SC3. Nth treatment device 110N has an Nth SIM card SCN.

Each patient treatment device can be configured to communicate with a computer of the processor system 130S, for example a personal computer (hereinafter "PC") to upload patient data, although the data can be uploaded in many additional ways, for example with a cell phone. First patient treatment device 110A can be connected to a first PC 162. Second patient treatment device 110B can be connected to a second PC 164. Third patient treatment device 110C can be connected to a third PC 166. Nth patient treatment device 110N can be connected to an Nth PC 168. Data can be transferred from each treatment device to the processor system in many ways, for example electronic serial ports, cables, memory devices such as universal serial bus (hereinafter "USB") memory sticks, infrared optical link, modem, wireless local radio such as Bluetooth™. The communication link may also provide software updates to the treatment device. The patient specific module may also be used to transfer the subjective patient data. For example, the patient specific module may comprise a USB memory stick configured to upload patient data to the processor system and download additional treatments from the processor system, such that patient specific module can permit additional treatments when inserted into the treatment device after the patient data are uploaded.

Each PC may comprise a corresponding display for the patient to view and annotate the patient data. First PC 162 may comprise a first display 162D. Second PC 164 may comprise a second display 164D. Third PC 166 may comprise a third display 166D. Nth PC 168 may comprise an Nth display 168D. The patient can log into a website and upload the data to a remote server. The patient data can be annotated before being uploaded to the remote server, and may be annotated by the corresponding patient after being uploaded to the server.

Remote server 130 can be connected to the plurality of patient computers 160 to receive the patient data. Remote server 130 may comprise a plurality of servers. At least some statistical analysis can be performed on the patient data to determine treatment trends and results that can be presented as meta data 132 without patient identities so as to maintain patient confidentiality.

Remote server 130 can be connected to the plurality of physician computers 140. The plurality of physician computers may comprise a first computer 142 (hereinafter "DPC1"), comprise a second computer 144 (hereinafter "DPC2"), a third computer 146 (hereinafter "DPC3"), an Nth computer 148 (hereinafter "DPCN"). Each of the physician computers can be used by a physician to view data from his or her own patients. Each physician can view his or her respective computer, for example first physician 152 and first computer 142, second physician 154 and second computer 144, third physician 156 and third computer 146, and Nth physician 158 and Nth computer 148. For example, remote server 130 can be connected to the plurality of physician computers 140 so as to transmit patient data to a physician when the physician is logged into the system such that data from his or her patients is available for the physician to view. The physician may also view meta data from the patient population to compare the results of his patients to other patients. The physician can select a treatment for the patient identified and displayed on his or her computer, and the patient identifier and treatment can be combined when sent to the patient specific module to ensure that the selected treatment is combined with the identified patient, such that the correct treatment is delivered to the correct patient.

The processor system can be connected to SIM card writer 134 to write patient treatments onto a SIM card, for example SIM card SCX. SIM card SCX can be similar to the PSM and SIM card, as described above. The SIM card may be programmed and shipped to the patient. Alternatively or in combination, the SIM card can be written at many locations, for example at least one of a pharmacy or the physician's office. SIM card writer 134 can write to a plurality of SIM cards. Each SIM card can be provided to a one patient, such that the patient can insert the SIM card into the patient treatment device to receive treatment.

FIG. 1D1 shows a program 132SP of the processor system 130S of the system for diagnosing and treating patients as in FIG. 1D. The program 132SP may comprise instructions embodied in tangible medium 132M of the processor system, such that processor system 130S comprising tangible medium 132M is configured to implement the instructions of program 132SP. Program 132SP comprises an input routing 132SI, and output routine 132SO and a run routine 132SR. Input routine 132SI and output routine 132SO are each operatively coupled to run routine 132SR. Input routine 132SI may comprise an input routine, for example an input module, configured couple to a source of subjective patient, for example configured to couple to each of the patient treatment devices to receive subjective patient data from each of the patients. The run routine 132SR may comprise a patient data module, a metadata analysis module, a physician display module, and a patient treatment module. The patient data module may store patient data from the treatment devices. The metadata analysis module may transform the patient data to metadata, as described above. The physician display module may prepare the metadata from the patient population and individual patient data, such that the combined data are ready to be output to a physician display. The patient treatment module may comprise software configured to prepare the patient treatment information and patient identifier information on the physician display. The patient treatment module can be configured to receive patient information to treat the patient from the display. The patient treatment module can also be configured to prepare patient treatment instructions for the patient specific module of a specific patient. Output module 132SO is operationally coupled to the run routine to output the information and treatment parameters processed by the run routine 132SR.

It should be appreciated that the specific modules and/or routines shown in FIG. 1D1 provide a particular configuration of the computer program 132SP, according to some embodiments of the present invention. The individual modules and/or routines illustrated in FIG. 1D1 may include multiple subroutines that may be performed in various sequences as appropriate to the individual module and/or routine. Furthermore, additional modules and/or routines may be added or removed depending on the particular applications. One of ordinary skill in the art would recognize many variations, modifications, and alternatives.

Figure 2A:
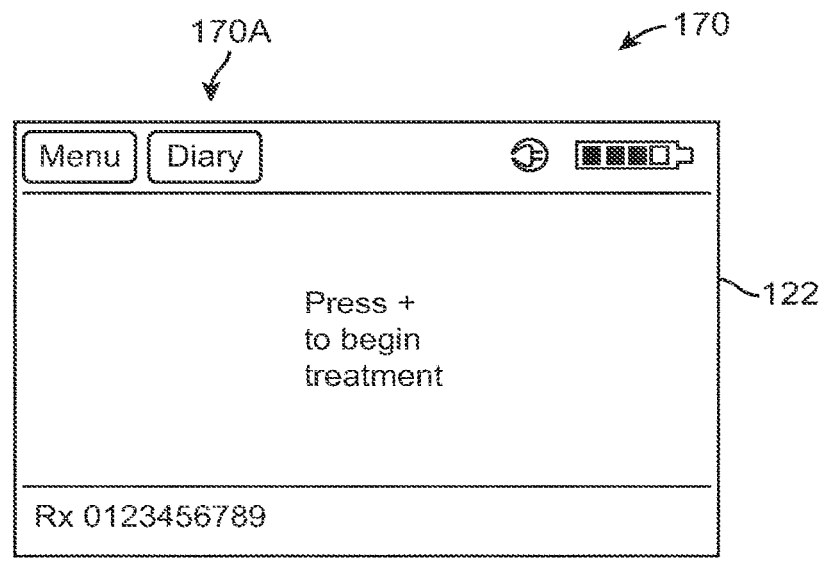
FIG. 2A shows the hand held treatment device as in FIGS. 1A-1D with instructions for treatment and journal entries shown on the display.

FIG. 2A shows the hand held treatment device as in FIGS. 1A-1D with instructions 170 for treatment and journal entries shown on display 122. Instructions 170 may comprise selection icons 170A for the patient to select a menu or a diary. When the patient selects menu, the patient is directed, for example, to a screen with a menu of options including patient information. When the patient selects diary, the patient is directed to a series of screens to record subjective patient data indicating how the patient is feeling.

Figure 2B:
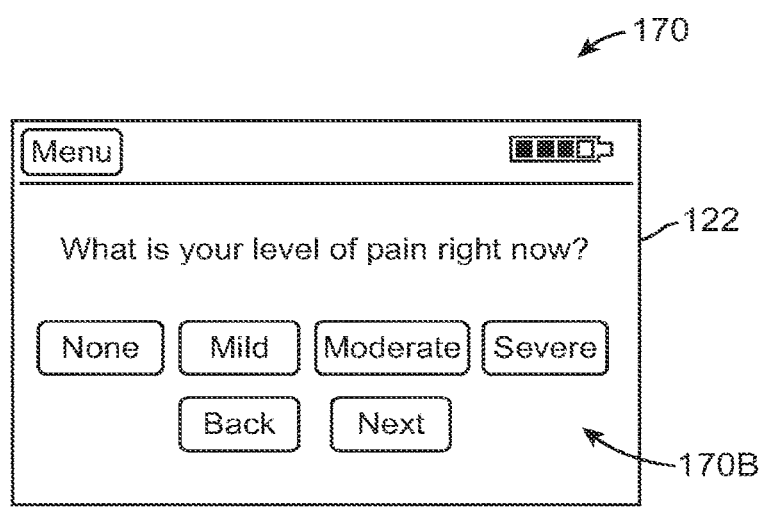
FIG. 2B shows the hand held treatment device as in FIG. 2A with a journal entry menu for pain shown on the display.

FIG. 2B shows the hand held treatment device as in FIG. 2A with a journal selection menu for pain 170B shown on the display 122. The journal selection menu for pain 170B comprises a plurality of icons to determine the level of patient pain, for example none, mild, moderate and severe. The menu also includes icons to go back and to move forward to the next screen.

Figure 2C:
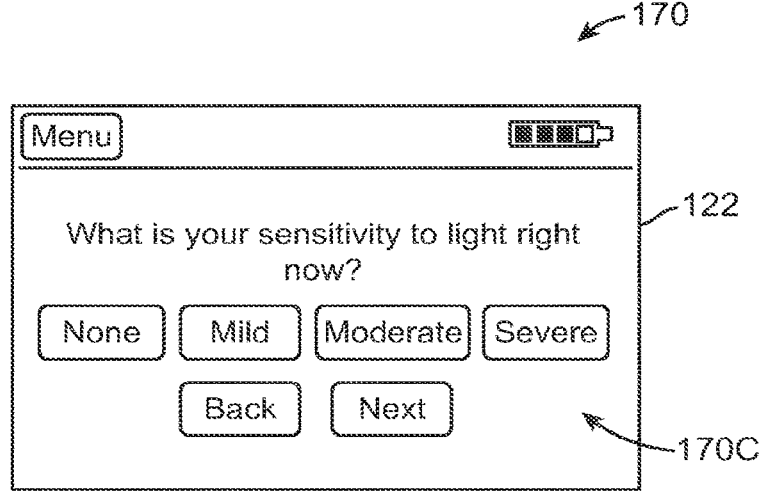
FIG. 2C shows the hand held treatment device as in FIG. 2A with a journal entry menu for sensitivity to light shown on the display.

FIG. 2C shows the hand held treatment device as in FIG. 2A with a journal entry menu for sensitivity to light 170C shown on the display 122. The journal selection menu for sensitivity to light 170C comprises a plurality of icons to determine the level of patient sensitivity to light, for example none, mild, moderate and severe. The menu also includes icons to go back and to move forward to the next screen. Patient sensitivity to light can also be referred to as photophobia.

Figure 2D:
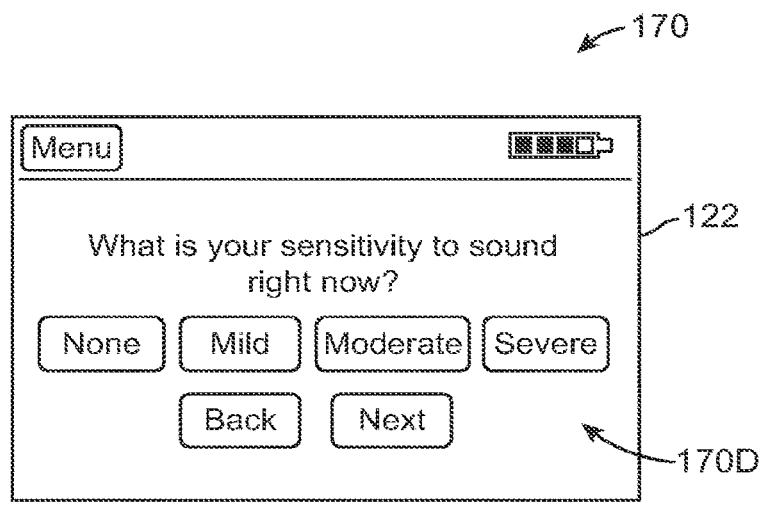
FIG. 2D shows the hand held treatment device as in FIG. 2A with a journal entry menu for sensitivity to sound shown on the display.

FIG. 2D shows the hand held treatment device as in FIG. 2A with a journal entry menu for sensitivity to sound 170D shown on the display 122. The journal selection menu for sensitivity to sound 170D comprises a plurality of icons to determine the level of patient sensitivity to sound, for example none, mild, moderate and severe. The menu also includes icons to go back and to move forward to the next screen. Patient sensitivity to sound can also be referred to as phonophobia.

Figure 2E:
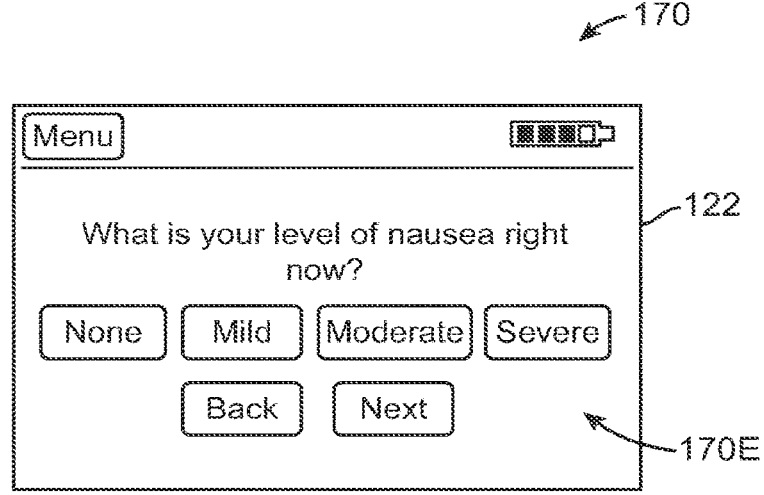
FIG. 2E shows the hand held treatment device as in FIG. 2A with a journal entry menu for nausea shown on the display.

FIG. 2E shows the hand held treatment device as in FIG. 2A with a journal entry menu for nausea shown on the display. The journal selection menu for nausea 170D comprises a plurality of icons to determine the level of patient nausea, for example none, mild, moderate and severe. The menu also includes icons to go back and to move forward to the next screen.

Figure 2F:
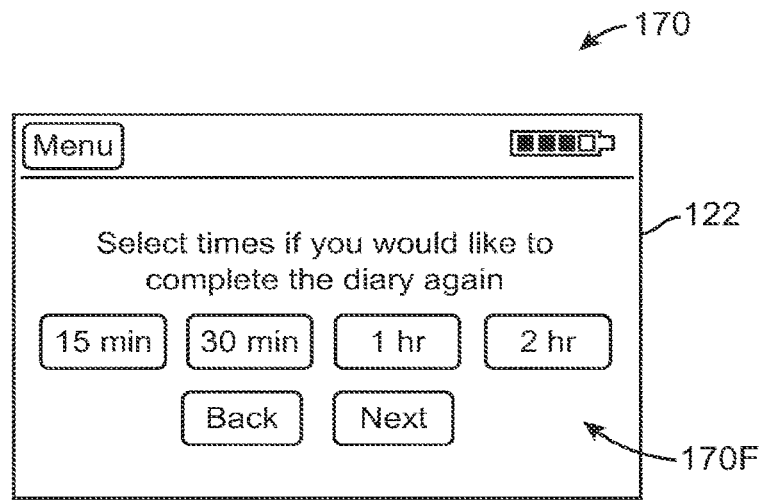
FIG. 2F shows the hand held treatment device as in FIG. 2A with a journal entry menu for pain shown on the display.

FIG. 2F shows the hand held treatment device as in FIG. 2A with a journal entry menu with icons to select times for completing the diary again to collect additional patient data at a later time of 15 min., 30 min., 1 hr., 2 hr. The patient can select the Back icon to go back, for example to the selection menu for nausea. When the patient selects next the patient can be taken back to a treatment screen with an icon indicating how to receive treatment, for example as shown in FIG. 2A.

FIG. 2G shows the treatment history and journal information shown on a display of a processor system 130S as in FIG. 1D for review by at least one of the patient or the physician. For example, the patient can view his or her data on display 162 D prior to uploading the data. The patient may also view the data when the patient is logged into the web site after the data are uploaded. The patient can annotate the data. The physician can view similar data screens for each of his patients. The physician may also view meta data and statistical trends from all of the patients in the system when such data is presented to maintain patient confidentiality for patients in the system not under care of the physician viewing the data.

The user interface may be configured in many ways as an alternative or in combination with the icons shown on the display as in FIGS. 2A to 2G. For example, the patient interface may comprise discreet buttons or switches located near the display such that the definition of each switch may change with the context of the question on the screen. For example, six buttons may be located near the screen such that the patient can select the button corresponding to the associated text on the display corresponding to a patient selection of "none", "mild", "moderate", "severe", "back" or "next". The patient interface may also comprise a display and a separate keyboard, in which the patient types the response to each question. The patient interface may also comprise the display and mouse, in which the patient clicks on the desired response. The patient interface may also comprise a voice response system in which the device asks a question and the patient replies verbally or selects a particular key as a response.

FIG. 3 shows a method 300 of treating a patient for a neurological disorder with system as in FIGS. 1A to 2G. Method 300 can be implemented with the treatment device and processor system, as described above. A step 305 presents a menu to a patient with a menu selection to enter data in the diary or receive treatment. The menu shown to the patient at step 305 may also include menu a selection to view additional menus. A step 310 treats the patient for the neurological disorder with a magnetic field and time stamps the time and date of the treatment to a non-volatile memory, as described above. The patient may be treated for a migraine headache. A step 315 enters subjective patient data, and the patient may enter this data directly into the treatment device, as described above. The subjective patient data may comprise symptoms, for example known symptoms of migraines such as aura the associated symptoms of aura. The subjective patient data may also include data related to migraine triggers, for example environmental triggers such as load noises. A sub step 315A presents pain levels on the display for the patient to select one level. A sub step 315B presents photophobia levels on the display for the patient to select one level. A sub step 315C presents phonophobia levels on the display for the patient to select one level. A sub step 315D presents nausea levels on the display for the patient to select one level. A step 320 time stamps the subjective patient data to correspond to a time and date when the subjective patient data are entered. A step 325 present a menu selection for the patient to enter subjective patient data again later, for example 15 minute later as described above. A step 330 enters subjective patient data a second time, for example similar to step 315 and sub steps 315A to 315D. A step 335 time stamps the patient data from step 330 with a second time stamp corresponding to the time and date at which the data are entered for step 330. A step 340 connects the patient treatment device to a patient computer, for example a patient personal computer or a patient hand held device. A step 345 logs the patient onto a website. A step 350 uploads the patient and treatment data from the treatment device to a server where patient data from a plurality of patient are stored. A step 355 reviews and annotates the patient data, for example review and annotation by the patient. A step 360 reviews the patient data, for example review by a physician. A step 365 compares the patient data with meta data from the plurality of patients, for example a comparison by the physician. A step 370 determines treatment parameters to treat the patient, for example treatment parameters of a treatment plan determined by the physician. A step 375 writes the treatment parameters of the treatment plan to a patient specific module, or PSM, as described above. The treatment parameters, for example the treatment plan, may comprise commands to the treatment device, as described above. A step 380 transports the PSM to the patient treatment device. A step 385 inserts the PSM into the patient treatment device. A step 390 treats the patient in response to the patient treatment parameters, for example with treatment commands stored on the PSM in accordance with the treatment plan. A step 395 repeats the above steps.

It should be appreciated that the specific steps illustrated in FIG. 3 provide a particular method of treating a neurological disorder, according to some embodiments of the present invention. Other sequences of steps may also be performed according to additional embodiments. For example, additional embodiments of the present invention may perform the steps outlined above in a different order. Moreover, the individual steps illustrated in FIG. 3 may include multiple sub-steps that may be performed in various sequences as appropriate to the individual step. Furthermore, additional steps may be added or removed depending on the particular applications. One of ordinary skill in the art would recognize many variations, modifications, and alternatives.

While the foregoing invention has been described in some detail for purposes of clarity and understanding, it will be clear to one skilled in the art from a reading of this disclosure that various changes in form and detail can be made without departing from the true scope of the invention. The above examples are provided to illustrate the invention, but not to limit its scope; other variants of the invention will be readily apparent to those of ordinary skill in the art and are encompassed by the claims of the invention. The scope of the invention should, therefore, be determined not with reference to the above description, but instead should be determined with reference to the appended claims along with their full scope of equivalents.

What is claimed is:

1. A method for prophylactic treatment for migraine headaches in a patient, the method comprising:
   positioning a handheld treatment device adjacent to the patient's head, the handheld treatment device consisting of a casing containing:
   a processor, circuitry operatively coupled to the processor, the circuitry comprising a coil configured to generate an electromagnetic field, a patient interface operatively coupled to the processor, the patient interface comprising a visual indication of a prescription that confirms the handheld treatment device is available for the patient to use to provide a limited number of treatments according to a treatment plan, and a buzzer operatively coupled to the processor, the buzzer configured to generate an alert indicating that it is time for a treatment of the limited number of treatments;

generating, by the buzzer, the alert;

upon the generation of the alert by the buzzer, initiating the treatment by directing one or more pulses of the electromagnetic field toward the patient's head, wherein the positioning and directing are performed at least once per day according to the treatment plan;

selecting, by the patient, one or more icons displayed via an electronic diary that is configured to track usage of the device, the one or more icons comprising pre-set levels of severity of one or more categories of subjective data related to the patient; and adjusting the treatment plan based on the usage of the device and the selected one or more icons.

2. The method of claim 1, wherein the treatment plan is written into a patient specific module coupled to the processor.

3. The method of claim 2, wherein the patient specific module comprises a subscriber identity module (SIM).

4. The method of claim 1, wherein the positioning and directing are performed only once per day.

5. The method of claim 1, wherein the treatment plan specifies a number of the one or more pulses of the electromagnetic field to be directed.

6. The method of claim 5, wherein the number is two.

7. The method of claim 1, wherein the one or more categories of subjective data comprise pain, sensitivity to light, sensitivity to sound, nausea, aura, and neck stiffness.

8. The method of claim 1, wherein the electronic diary further comprises one or more of a treatment history, episode symptoms and medications, and a headache diary.

9. The method of claim 1, wherein the buzzer is further configured to generate an alert indicating that it is time for the patient to enter additional information into the electronic diary.

* * * * *